US012765804B2

(12) United States Patent
Zhou et al.

(10) Patent No.: US 12,765,804 B2
(45) Date of Patent: Oct. 20, 2026

(54) ANORECTAL BIOFEEDBACK DEVICE

(71) Applicant: Western Sydney University, Penrith (AU)

(72) Inventors: Jerry Zhou, Penrith (AU); Bahman Javadi, Penrith (AU); Vincent Ho, Penrith (AU); Eric Siu, Penrith (AU); Lloyd Coleman, Penrith (AU); Barbara Van de Sande, Penrith (AU); Bill Karabetsos, Penrith (AU)

(73) Assignee: Western Sydney University, Penrith (AU)

( * ) Notice: Subject to any disclaimer, the term of this patent is extended or adjusted under 35 U.S.C. 154(b) by 1048 days.

(21) Appl. No.: 17/757,698

(22) PCT Filed: Dec. 18, 2020

(86) PCT No.: PCT/AU2020/051398
§ 371 (c)(1),
(2) Date: Jun. 17, 2022

(87) PCT Pub. No.: WO2021/119757
PCT Pub. Date: Jun. 24, 2021

(65) Prior Publication Data

US 2023/0037389 A1 Feb. 9, 2023

(30) Foreign Application Priority Data

Dec. 19, 2019 (AU) ................................ 2019904832

(51) Int. Cl.

| | |
|---|---|
| ***A61B 5/11*** | (2006.01) |
| ***A61B 5/00*** | (2006.01) |
| ***A61B 5/22*** | (2006.01) |

(52) U.S. Cl.
CPC ............ *A61B 5/1107* (2013.01); *A61B 5/227* (2013.01); *A61B 5/486* (2013.01); *A61B 5/72* (2013.01); *A61B 2562/0247* (2013.01)

(58) Field of Classification Search
CPC ......... G01L 23/10; A61B 5/073; A61B 5/076; A61B 5/6861; A61B 2650/0209
See application file for complete search history.

(56) References Cited

U.S. PATENT DOCUMENTS 5,674,238 A * 10/1997 Sample .................. A61B 5/227 606/192
5,924,984 A 7/1999 Rao (Continued)

FOREIGN PATENT DOCUMENTS

| | | |
|---|---|---|
| CN | 207532394 U | 6/2018 |
| JP | 2002143133 A | 5/2002 |

(Continued)

OTHER PUBLICATIONS

Extended European Search Report issued in European Application No., 20902139.3, dated Dec. 13, 2023.

(Continued)

*Primary Examiner* — Alex M Valvis
(74) *Attorney, Agent, or Firm* — Knobbe, Martens, Olson & Bear, LLP

(57) ABSTRACT

A pressure sensing device including an elongate housing configured to be at least partially inserted into a user, and that defines an external surface having a proximal end and a distal end defining a longitudinal axis therebetween. The device includes a first pressure sensor, configured to sense pressure applied to a first portion of the external surface and to convert the sensed pressure to first pressure data, and a second pressure sensor, configured to sense pressure applied to a second portion of the external surface and to convert the sensed pressure to second pressure data. Sensor is spaced, (Continued)

along the longitudinal axis, toward the distal end from sensor.

15 Claims, 10 Drawing Sheets

(56) References Cited

U.S. PATENT DOCUMENTS

| | | | | |
|---|---|---|---|---|
| 8,758,387 | B2 | 6/2014 | Rao et al. | |
| 9,046,435 | B2 * | 6/2015 | Vagle | G01L 19/0645 |
| 9,724,036 | B2 | 8/2017 | Broens | |
| 2008/0221484 | A1 | 9/2008 | Sarvazyan et al. | |
| 2009/0222058 | A1 | 9/2009 | Craggs | |
| 2013/0018308 | A1 * | 1/2013 | Rao | A63B 71/0622 604/99.04 |
| 2014/0066813 | A1 | 3/2014 | Daly et al. | |
| 2017/0119267 | A1 | 5/2017 | Joo et al. | |
| 2018/0146892 | A1 | 5/2018 | Billard | |
| 2018/0214063 | A1 | 8/2018 | Nielsen et al. | |

FOREIGN PATENT DOCUMENTS

| | | | | |
|---|---|---|---|---|
| JP | 2019528103 A | * 10/2019 | A61B 5/4431 |
| KR | 101325581 B1 | 11/2013 | |

OTHER PUBLICATIONS

International Search Report in PCT/AU2020/051398 issued Mar. 1, 2022.

Written Opinion of the International Searching Authority in PCT/AU2020/051398 issued Mar. 1, 2022.

Chinese Office Action for Application No. 202080094711.3 dated Jan. 13, 2025 (in 24 pages).

* cited by examiner

ANORECTAL BIOFEEDBACK DEVICE

CROSS-REFERENCE TO RELATED APPLICATIONS

The present application claims priority from Australian Provisional Patent Application No 2019904832 filed on 19 Dec. 2019, the contents of which are incorporated herein by reference in their entirety.

TECHNICAL FIELD

The present disclosure relates, generally, to devices for sensing pressure, and, more particularly, to a pressure sensing device configured to be inserted into a user.

BACKGROUND

Pressures are prevalent throughout the body and include blood pressure, eye pressure, intrathoracic pressure, and anorectal pressure.

Bowel problems, such as faecal incontinence and/or chronic constipation may come about due to weak or otherwise suboptimal performance of anorectal muscles, for example resulting from damage caused by pregnancy, surgery or radiation therapy. Such bowel problems may also be caused by poor coordination between anorectal muscles. Anorectal muscles involved in faecal incontinence and/or chronic constipation include the anal sphincter and the muscles which produce rectal pressure.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Disclosed herein is a pressure sensing device, comprising:

- an elongate housing configured to be at least partially inserted into a user, the elongate housing defining an external surface and having a proximal end and a distal end defining a longitudinal axis therebetween, the distal end being the leading end of the housing in a direction of insertion of the housing into the user;
- a first pressure sensor configured to sense first pressure applied to a first portion of the external surface and to convert the sensed first pressure to first pressure data; and
- a second pressure sensor configured to sense second pressure applied to a second portion of the external surface and to convert the sensed second pressure to second pressure data, the second pressure sensor spaced, along the longitudinal axis, toward the distal end from the first pressure sensor.

The first pressure sensor may be configured to sense anal sphincter pressure applied to the first portion of the external surface and the second pressure sensor may be configured to sense rectal pressure applied to the second portion of the external surface.

The first portion may have a length, measured along the longitudinal axis, of between around lcm and around 6 cm, or of between around 2 cm and around 6 cm, or of between around 3 cm and around 5 cm, or of around 4 cm. The second portion may have a length, measured along the longitudinal axis, of up to around 3 cm or of up to around 2 cm or of up to around lcm. The length of the first portion may be defined by a first pressure pad associated therewith, the first pressure pad being configured to transfer the first pressure applied thereto to the first pressure sensor. The length of the second portion may be defined by a second pressure pad associated therewith, the second pressure pad being configured to transfer the second pressure applied thereto to the second pressure sensor. The spacing, along the longitudinal axis, between the second pressure sensor and the first pressure sensor, or between the centre of the first portion and the centre of the second portion, between approximately 3 cm and approximately 8 cm, or between approximately 4 cm and approximately 6 cm or between approximately 4 cm and approximately 5 cm. A first projection may extend from the first pressure pad toward the first pressure sensor, wherein the first pressure applied to the first pressure pad is transferred to the first pressure sensor via the first projection. A second projection may extend from the second pressure pad toward the second pressure sensor, wherein the second pressure applied to the second pressure pad is transferred to the second pressure sensor via the first projection. The first pressure pad may be relatively rigid so as not to deform in response to application of the first pressure thereto. The second pressure pad may be relatively rigid so as not to deform in response to application of the second pressure thereto. The device may comprise one or more pressure sensor in addition to the first and second pressure sensor. The one or more pressure sensor may be positioned at a respective one or more different location along the longitudinal axis to the first and second pressure sensors so as to sense pressure applied to a respective one or more portion of the external surface, the respective one or more portion being spaced, along the longitudinal axis, from the first and second portions of the external surface. The first pressure pad may be resiliently biased away from the first pressure sensor to cause the first pressure pad to return to an "at rest" configuration upon removal of external pressure applied to the first portion of the external surface. The second pressure pad may be resiliently biased away from the second pressure sensor to cause the second pressure pad to return to an "at rest" configuration upon removal of external pressure applied to the second portion of the external surface.

The pressure sensing device may comprise a spine extending along at least that portion of the elongate housing comprising the first portion of the external surface and the second portion of the external surface. The first pressure sensor and the second pressure sensor may be fixedly connected relative to the spine, for example by being mounted on the spine.

The pressure sensing device may further comprise a transmitter carried by the housing, the transmitter being configured to transmit the first pressure data and the second pressure data. The transmitter may be carried by a portion of the device that is disposed externally of the user, in use. The transmitter may be configured to wirelessly transmit the first pressure data and the second pressure data, such as via Bluetooth.

The pressure sensing device may comprise a rechargeable power source.

The external surface of the housing may have a shape configured to cause the first pressure sensor to automatically align with the user's anal sphincter upon insertion of the housing into the user. The first portion may define a waist portion of the shape. The pressure sensing device may comprise a flange extending outwardly in a direction transverse to the longitudinal axis, the flange being configured to abut a portion of the user upon insertion of the housing into the user and thereby to limit the extent of insertion of the housing into the user. The position, along the longitudinal axis, of the flange relative to the first pressure sensor may be such that, in use, abutment of the flange with the portion of the user facilitates alignment of the first pressure sensor with the user's anal sphincter.

The device may further comprise an inflatable element carried by the distal end of the elongate housing. The inflatable element may be connectable to a fluid source, such as via a port at the proximal end, for inflating the inflatable element. The device may comprise a pump for pumping fluid from the fluid source into the inflatable element.

Also disclosed is a pressure sensing system, comprising:

the pressure sensing device as defined in any one of paragraphs [0006] to [0013] above; and a computer configured to receive and process the first pressure data and the second pressure data from the pressure sensing device.

The processing of the pressure data by the computer may comprise processing to assess the magnitude of pressure applied to the first and second sensors and/or the timing of pressure applied to the first and second sensors. The processing of the pressure data by the computer may comprise processing to determine whether the magnitude and/or timing of pressure applied to the first and second sensors meets predetermined criteria.

The pressure sensing system may comprise a user interface associated with the computer and configured to present information associated with the first pressure data and the second pressure data received from the pressure sensing device to the user. The information associated with the pressure data received from the pressure sensing device may comprise information on whether the pressure data indicates that the magnitude and/or timing of pressure applied to the first and second sensors meets predetermined criteria.

The computer may be further configured to receive data inputs from the user and to process the received data inputs along with the first pressure data and the second pressure data. The received data inputs may comprise at least one of: food intake of the user; water intake of the user; physical exercise performed by the user; and properties of stools produced by the user.

The pressure sensing system may further comprise a server communicatively connected to the computer for receiving pressure data. The computer may be further configured to generate a report of the user's progress. The pressure sensing system may further comprise a charging dock for charging the rechargeable power source.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the disclosure will now be described by way of example only with reference to the accompanying drawings in which.

DETAILED DESCRIPTION OF EXEMPLARY EMBODIMENTS

Figure 1:
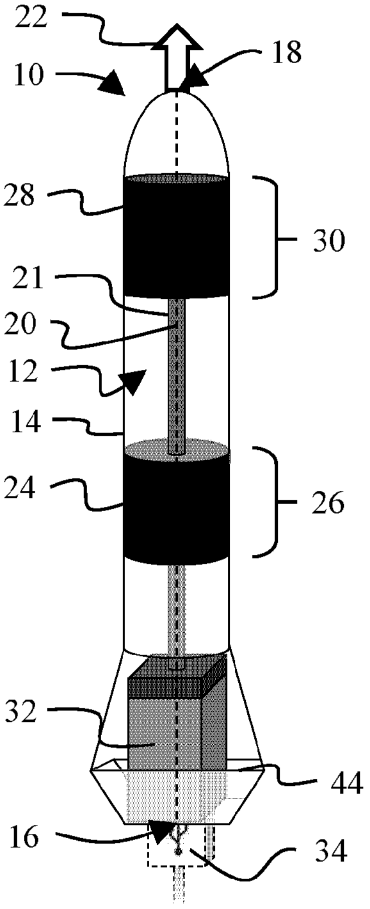
FIG. 1 shows an embodiment of a pressure sensing device.

In the drawings, reference numeral 10 designates a pressure sensing device (FIG. 1). The pressure sensing device 10 comprises an elongate housing 12 configured to be at least partially inserted into a user, and defines an external surface 14 having a proximal end 16 and a distal end 18 defining a longitudinal axis 20 therebetween. The distal end 18 is the leading end of the housing 12 in a direction of insertion 22 of the housing 12 into the user.

The pressure sensing device 10 further comprises a first pressure sensor 24 configured to sense pressure applied to a first portion 26 of the external surface 14 and to convert the sensed pressure to first pressure data. The pressure sensing device 10 further comprises a second pressure sensor 28 configured to sense pressure applied to a second portion 30 of the external surface 14 and to convert the sensed pressure to second pressure data. The first and the second pressure sensor 24, 28 may each comprise a solid state pressure sensor and a transducer to enable the conversion of the sensed pressure to pressure data. In other embodiments, strain gauges may be used instead of the solid state pressure sensors. The first pressure sensor 24 and the second pressure sensor 28 may be communicatively connected via a wire (not shown) carried by a conduit 21, or wirelessly.

The second pressure sensor 28 is spaced, along the longitudinal axis 20, toward the distal end 18 from the first pressure sensor 24. The spacing of the second pressure sensor 28 from the first pressure sensor 24 along the longitudinal axis 20 is between approximately 5 cm and 8 cm, preferably between approximately 5 cm and 6 cm. In this embodiment, the spacing is implemented such that the first pressure sensor 24 is configured to sense anal sphincter pressure applied to the first portion 26 of the external surface 14, and the second pressure sensor 28 is configured to sense rectal pressure applied to the second portion 30 of the external surface 14.

Device 10 further comprises a transmitter 32 carried by the housing 12 and being configured to transmit the first pressure data and the second pressure data. In this embodiment, the transmitter 32 is configured to wirelessly transmit the first pressure data and the second pressure data via Bluetooth. It will be understood by the person skilled in the art that the first pressure data and the second pressure data may be transmitted by the transmitter 32 as a single packet of data or as two separate packets of data. It will also be understood that, in other embodiments, the first pressure data and the second pressure data may be transmitted as an electrical signal through a wire.

The pressure sensor 10 further comprises a power source, for example, a battery (not shown), which, in this embodiment, is rechargeable, for example, by inserting a universal serial bus (USB) male connector 34 into a USB female receptacle carried by the housing 12 (not shown), which is configured to deliver power from the USB male connector 34 to the rechargeable battery.

Figure 2:
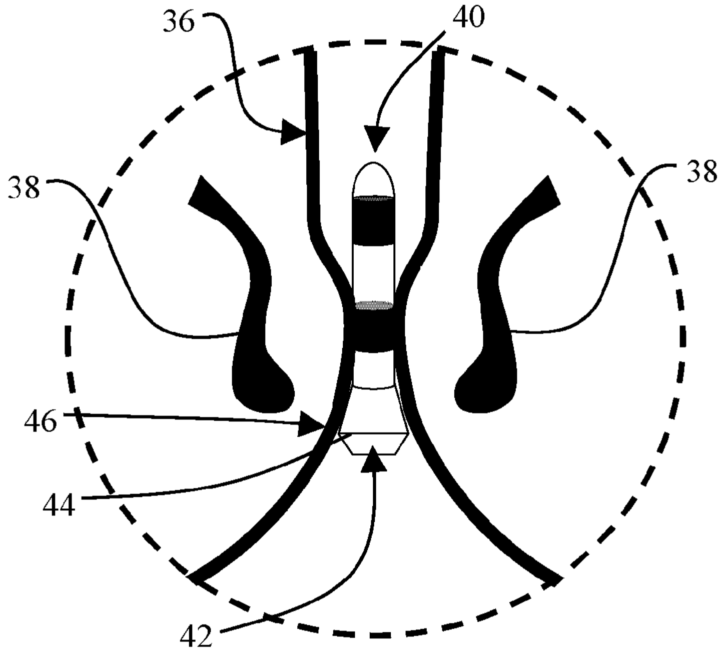
FIG. 2 shows the pressure sensing device shown in FIG. 1 in use.

Referring to FIG. 2, the pressure sensing device 10 is positioned in use within an anal cavity 36 of the user. The pressure sensing device is positioned such that the anal sphincter 38 is able to apply pressure to the first portion 26 of the external surface 14. The second portion 30 is located within the rectum 40 for sensing rectal pressure applied by the user.

To assist with the positioning of the pressure sensing device 10 in the user, the external surface 14 of the housing 12 has a shape configured to cause the first pressure sensor 24 to automatically align with the user's anal sphincter 38 upon insertion of the housing 12 into the user. For example, as shown in FIG. 2, a flange 44 of the pressure sensing device 10 extends outwardly in a direction transverse to the longitudinal axis 20 and is configured to abut a portion 46 of the user upon insertion of the housing 12 into the user, thereby limiting the extent of insertion of the housing 12 into the user. The position, along the longitudinal axis 20, of the flange 44 relative to the first pressure sensor 24 is such that, in use, abutment of the flange 44 with the portion 46 of the user facilitates alignment of the first pressure sensor 24 with the user's anal sphincter 38. Instead of, or in addition to flange 44, the first portion 26 may define a waist portion of the shape of the external surface 14 of housing 12, the waist portion being configured for engagement by the user's anal sphincter 38 upon insertion of the housing 12 into the user, thereby to align the first portion 26, and the first pressure sensor 24, with the user's anal sphincter 38. When the first portion 26 is aligned with the user's anal sphincter 38, the spacing between the first portion 26 and second portion 30 facilitates the second portion being located in the user's rectum 40 to sense rectal pressure. As also shown in FIG. 2, the transmitter 32 is carried by a portion 42 of the pressure sensing device 10 that is disposed externally of the user, in use.

The pressure sensing device 10 is suitable to sense manoeuvres or phases of the anorectal region of the user. The relative pressures of these phases in healthy users and unhealthy users with weak (incontinent) or hypertensive anorectal muscles are displayed in Table 1.

TABLE 1

Relative pressures for anorectal phases

| | Normal | Weak (e.g. incontinent) | Hypertensive (e.g. spasm) |
|---|---|---|---|
| Resting anal sphincter pressure (mmHg) | 40-70 | 0-39 | 71-200 |
| Max squeeze anal sphincter pressure (mmHg) | 100-180 | 20-90 | 181-500 |
| Bear down anal sphincter relaxation pressure (mmHg) | 20-60 | 0-39 | 61-200 |
| Bear down rectal contraction pressure (mmHg) | 60-120 | 0-59 | 121-390 |
| Bear down relaxation %* | ≥20% | <20% | <20% |

*Relaxation % is the anal sphincter pressure differential during bear down manoeuvre (an initial high-pressure squeeze then relaxation of the anal sphincter muscles).

Figure 4:
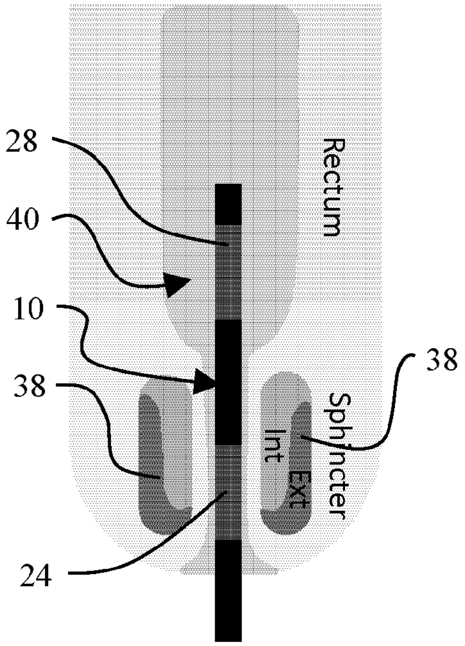
FIG. 4 shows a pressure schematic of the pressure sensing device shown in FIG. 1 in use during a relaxation phase.
Figure 5:
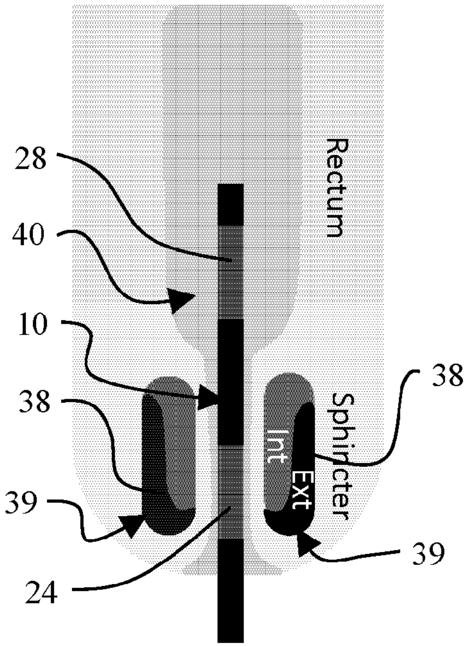
FIG. 5 shows a pressure schematic of the pressure sensing device shown in FIG. 1 in use during a squeezing phase.
Figure 6:
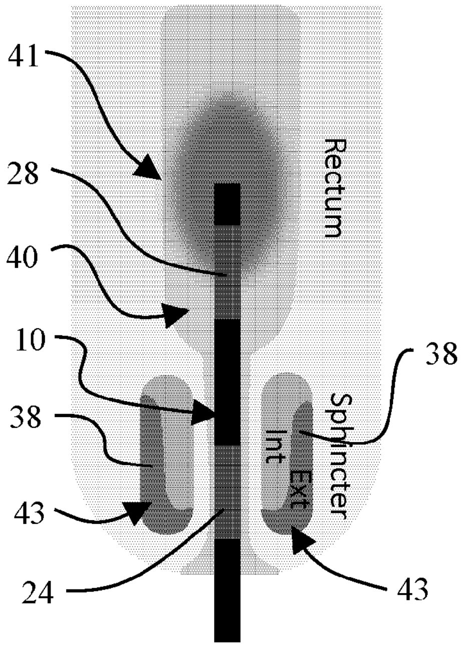
FIG. 6 shows a pressure schematic of the pressure sensing device shown in FIG. 1 in use during a pushing phase.

FIGS. 4-6 each show one phase in a healthy user with a schematic of the pressure sensing device 10 in use. FIG. 4 shows a resting phase of the user, with resting pressure being applied at the anal sphincter muscles 38 and in the rectum 40. FIG. 5 shows a squeezing phase, whereby the user is applying significant anal sphincter pressure to the first portion 26 of the pressure sensing device 10 as shown by a high pressure region 39, while the rectal pressure is maintained at the resting pressure, for example, to prevent stools from exiting the anal cavity 36 unintentionally. FIG. 6 shows a bear down phase, whereby the rectal pressure is increased as shown by a high pressure region 41, and the sphincter pressure is decreased below the resting sphincter pressure as shown by a low pressure region 43, for example, to allow the user to pass a stool.

However, unhealthy users with bowel problems, such as faecal incontinence and/or chronic constipation often will not display the pressures shown in the schematics of FIGS. 4-6. For example, users with bowel incontinence may have weak anal sphincter or rectal muscles, or both, and/or poor coordination between these muscles. In an attempt to treat such bowel problems, the pressure sensing device 10 may be used to facilitate training aimed at building the strength of the anal sphincter 38 and the muscles of the rectum 40, and improving coordination between these anorectal muscles, over time, and to monitor the effectiveness of such training, by providing anorectal biofeedback to the user and/or to a health professional treating the user.

Figure 3:
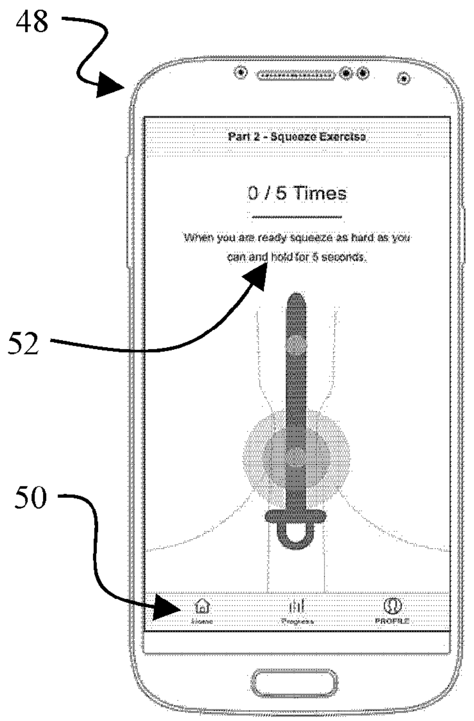
FIG. 3 shows a computer configured to receive and process pressure data from the pressure sensing device shown in FIG. 1.

To be useful for anorectal training purposes, the pressure sensing device 10 may be included as part of a pressure sensing system, which also includes a computer, for example a smartphone 48 or tablet computing device, configured to receive and process the first pressure data and the second pressure data from the pressure sensing device 10 (FIG. 3). It will be appreciated that the computer may be any other kind of computer and that the pressure sensing device 10 is not limited to use with the smartphone 48 or tablet computing device.

In one embodiment, the pressure sensing system is configured to determine an overall anorectal treatment progress to the user. To present this progress to the user, the processing of the pressure data by the smartphone 48 comprises processing to assess the magnitude of pressure applied to the first and second sensors 24, 28 and the timing/coordination of pressure applied to the first and second pressure sensors 24, 28. Further, the processing of the pressure data by the smartphone 48 comprises processing to determine whether the magnitude and timing/coordination of pressure applied to the first and second sensors 24, 28 meets predetermined criteria, such as, a target pressure, an average pressure, a maximum pressure, or a minimum pressure in the rectum 40 and/or the anal sphincter 38, and/or coordination of maximum pressure in the rectum 40 with minimum pressure in the anal sphincter 38. The predetermined criteria may also include a target number of squeezes or bear downs, or a maximum number of squeezes or bear downs. It will be appreciated by the person skilled in the art that a wide variety of predetermined training criteria may be used.

As seen in FIG. 3, a user interface 50 is associated with the smartphone 48 and is configured to present information associated with the pressure data received from the pressure sensing device to the user, such as training information 52, which may include a target magnitude, quantity and/or timing/coordination of the pressure applied to the pressure sensing device 10 by the user. The training information 52 may be a part of one or more training modules stored on the smartphone 48, which may be initiated by the user via the user interface 50 to begin a training session. The pressure data being received from the pressure sensing device 10 during training sessions completed by the user may be stored on the smartphone 48 to provide a performance history to the user via the user interface 50.

The treatment of bowel problems by anorectal muscle training may be supplemented by the diet of a user, for example, the fibre intake of the user, the water intake of the user, and the exercise performed by the user. Thus, in addition to the storing of the pressure data, the user may input data via the user interface 50 to be stored on the smartphone 48, such that the received data inputs from the user are processed along with the stored pressure data and/or the received first pressure data and the second pressure data. The received data inputs comprise at least one of: food intake of the user; water intake of the user; physical exercise performed by the user; and properties of stools produced by the user. The performance history and the user inputs including the properties of stools produced by the user, together provide the overall anorectal progress of the user to be presented and stored on the smartphone 48 via the user interface 50.

Figure 7:
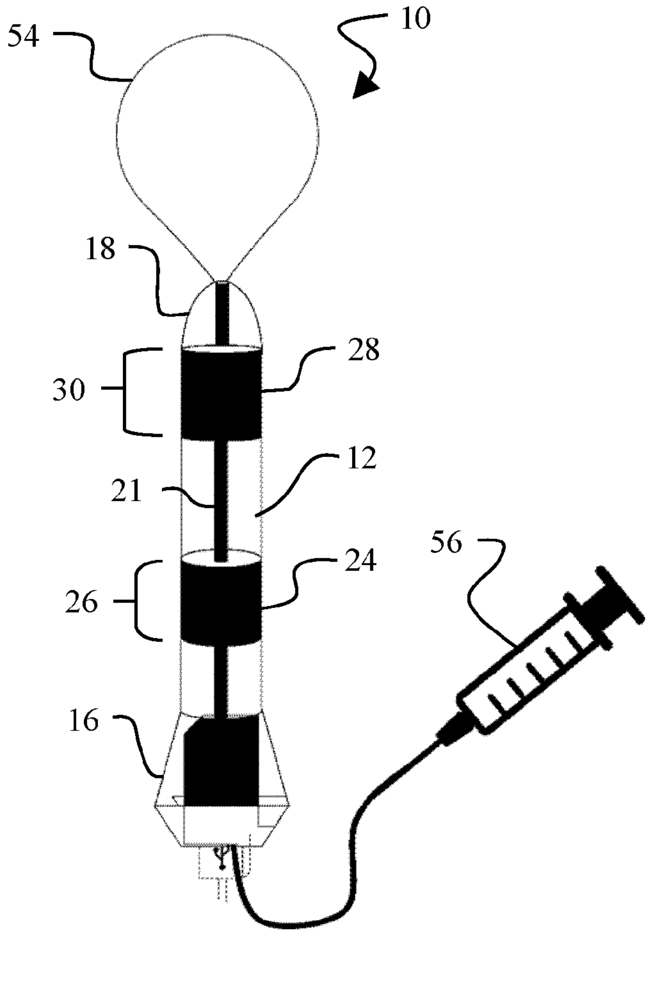
FIG. 7 shows another embodiment of the pressure sensing device, including an inflatable component.

FIG. 7 shows another embodiment of the pressure sensing device 10. Device 10 of FIG. 7 includes all of the features of device 10 described with reference to FIGS. 1-6, but also includes additional features as will now be described. An inflatable element in the form of a balloon 54 is carried by the distal end 18 of the pressure sensing device 10. The balloon 54 is connected to the conduit 21 which is configured to provide a fluid, such as air, to inflate the balloon 54. In this embodiment, air is provided to the balloon 54 using a pump 56, such as an external, manually operable syringe. Pump 56 is fluidly connected to the balloon 54 to pump fluid from an inlet port at the proximal end of the conduit 21. The balloon 54 is configured to be inflated with between approximately 20 cc and approximately 300 cc of fluid, depending on the patient's maximum generated anorectal pressure. In other embodiments, pump 56 may be onboard device 10. It will also be appreciated by the person skilled in the art that operation of the pump may be controlled by a machine. For example, the pump may be controlled via the interface 50 of the smartphone 48 to autonomously adjust the air pressure of the balloon 54 to suit the patient's training level.

Figure 8:
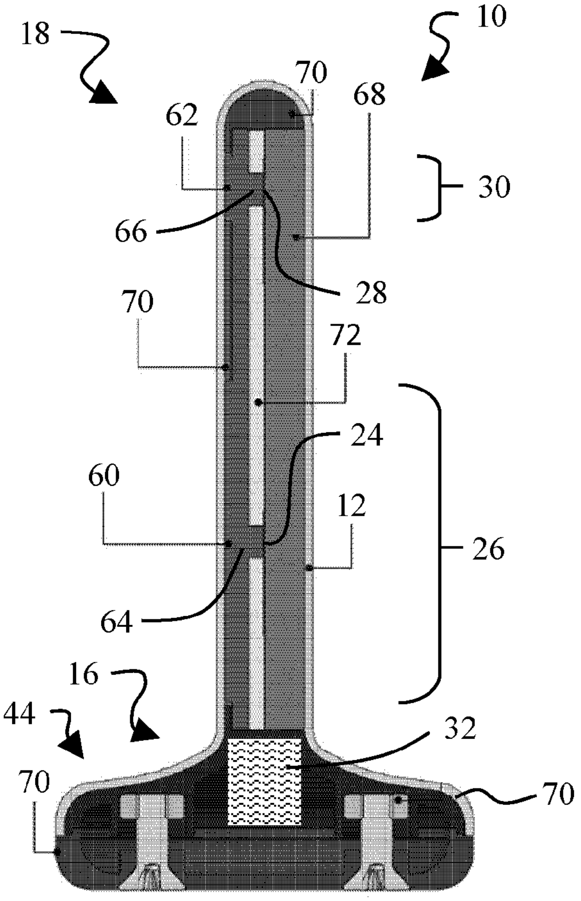
FIG. 8 shows yet another embodiment of the pressure sensing device.

FIG. 8 shows another embodiment of the pressure sensing device 10. Corresponding reference numerals are used to indicate features of device 10 of FIG. 8 that correspond with those of device 10 described with reference to FIGS. 1-6. In device 10 of FIG. 8, a length of first portion 26 is defined by a first pressure pad 60 and a length of second portion 30 is defined by a second pressure pad 62. A first projection 64 extends from first pressure pad 60 toward the first pressure sensor 24 and a second projection 66 extends from the second pressure pad 62 toward the second pressure sensor 28. Pressure applied to the first pressure pad 60 is transferred to the first pressure sensor 24 via the first projection 64 and pressure applied to the second pressure pad 62 is transferred to the second pressure sensor 28 via the second projection 66. Pressure pads 60, 62 are relatively rigid so as not to deform in response to application of anal sphincter pressure or rectal pressure. A spine 68 extends along the elongate housing 12, including along that portion thereof comprising the first portion 26 and the second portion 30. Pressure sensors 24, 28 are mounted on the spine 68. Spine 68, together with one or more other structural elements 70 fixedly connected thereto, defines a structural frame of device 10. Gaps 72 between pressure pads 60, 62 and spine 68 are filled with an elastically compressible material, such as neoprene, to maintain each of projections 64, 66 in alignment with its respective pressure sensor 24, 28. The elastically compressible material also biases pressure pads 60, 62 away from spine 68, and thereby projections 64, 66 away from the respective pressure sensors 24, 28, to cause pressure pads 60, 62 to return to an "at rest" configuration upon removal of external pressure applied to first and second portions 26, 30. In the FIG. 8 embodiment, housing 12 comprises a pliable coating, such as silicon, the coating being biocompatible in accordance with ISO 10993. Moreover, pressure pads 24, 28 and structural elements 70 and spine 68 are of a rigid plastics material, such as acrylonitrile butadiene styrene (ABS). However, it will be appreciated that the components of device 10 may be formed from any other suitable materials and that various components may be integrated, such as spine 68 and structural elements 70 being of integral, one-piece construction.

Figure 10:
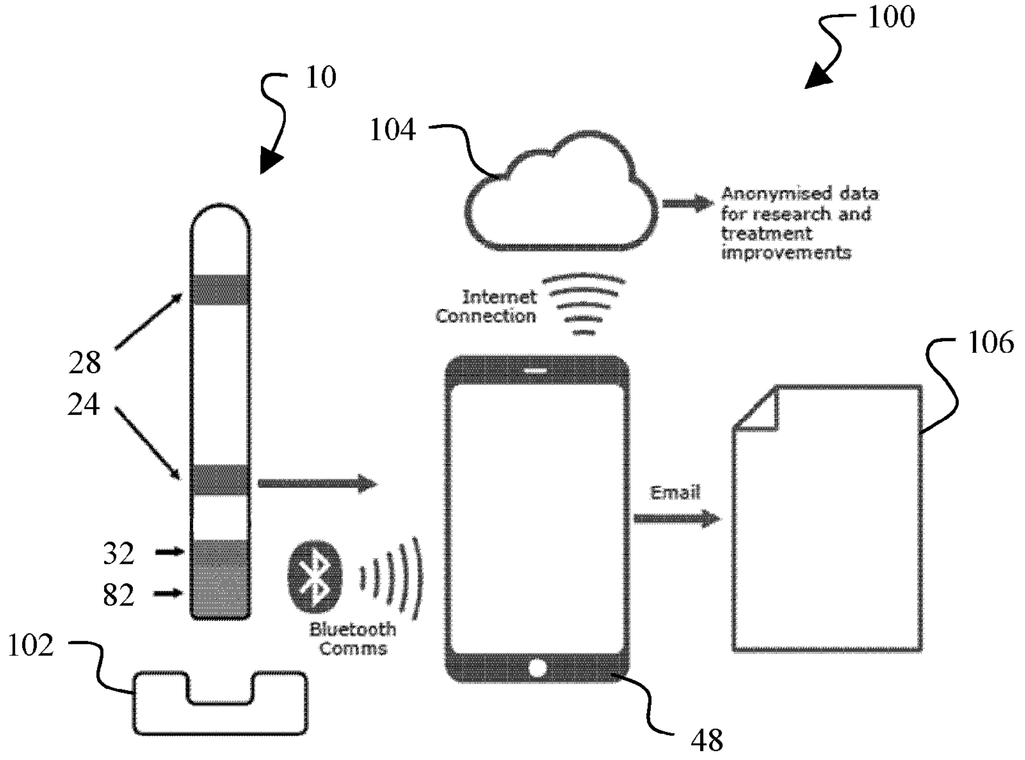
FIG. 10 shows a schematic of an embodiment of a pressure sensing system.

FIG. 10 shows a schematic of an embodiment of an anorectal training system or pressure sensing system 100, including device 10 with a battery 82 at the proximal end 16, a charging dock 102, the smartphone 48 and a server 104. The proximal end 16 is insertable into the charging dock 102 to recharge the battery 82 and the smartphone 48 is configured to communicate with the transmitter 32 of the device 10 via Bluetooth in order to receive pressure data to be stored on and/or retransmitted by the smartphone 48. In this embodiment, the user interface 50 (FIG. 3) also includes the option to generate a report 106 for the health professional to track the training progress of the patient, which, in this embodiment, is provided to the health professional via email. In addition, the pressure data may be anonymised and communicated to the server 104 via a wide area network for the purposes of research pending the patient's consent. It will be appreciated by the person skilled in the art that power may instead be provided to the pressure sensor 10 via the USB male connector 34, and that the generation of the report 106 and the communication with the server 104 may be excluded from the system 100.

In use, the user may insert the housing 12 of the pressure sensing device 10 into their own anal cavity 36 until the flange 44 abuts the portion 46 of the user, which will signify to the user that the pressure sensing device 10 is in a suitable position for use. It will be appreciated that the pressure sensing device 10 may also be inserted into the anal cavity 36 of the user by the health professional. The user may then initiate the user interface 50 on the smartphone 48 to begin a training session which requires the user, for example, to apply anal sphincter pressure on five consecutive occasions to the pressure sensing device 10 to complete the training session. The user or the health professional may then remove the housing 12 of the pressure sensing device 10 from the anal cavity 36 of the user. The user may then input their fibre intake, water intake, exercise performed, and their stool information to the smartphone 48 via the user interface 50. The user may then select an option via the user interface 50 to present the user's overall anorectal progress over time. The health professional may also observe the user's anorectal training progress over time via the user interface 50 to supervise the course of treatment.

Figure 9:
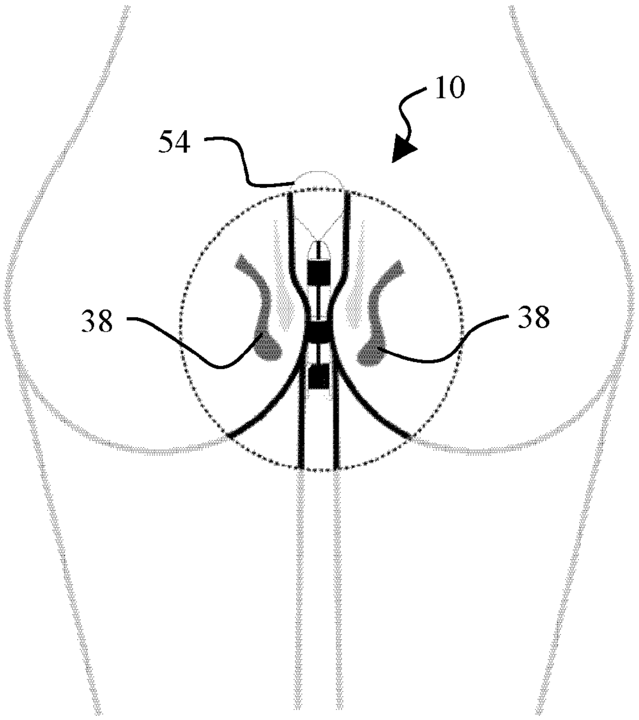
FIG. 9 shows the pressure sensing device shown in FIG. 7, in use.

FIG. 9 shows the embodiment of the pressure sensing device 10 of FIG. 7 in use. In addition to the use described in the previous paragraph, this embodiment allows for further training routines including simulated defecation, sensory training and urge resistance training. Simulated defecation requires the patient to attempt to expel the inflated balloon 54 filled, for example, with 50 cc of air, while the patient is in a squatted position. Sensory training involves progressively smaller balloon inflations until no sensation is felt by the patient, which is the patient's sensory threshold. The balloon 54 is deflated at this point to train the patient to perceive beyond their sensory threshold. Urge resistance training involves larger balloon inflations until a strong urge is experienced by the patient which is the patient's urge threshold. The balloon 54 is partially deflated at this point and the patient is instructed to use deep breathing techniques to counteract their urge sensation. It will be appreciated by the person skilled in the art that additional training routines may be conceptualised and added to the training program and/or the user interface 50 of the smartphone 48. It will also be appreciated that this embodiment of the pressure sensing device 10 may be incorporated into the anorectal training system 100, and that these additional training routines may either be completed by the patient with a health professional controlling the syringe 56 or by the patient alone using the smartphone 48 which remotely controls the pump 56 of the pressure sensing device 10.

Advantageously, the pressure sensing device 10, in use, simultaneously measures two distinct pressures, namely, rectal pressure and anal sphincter pressure. The simultaneous measurement of rectal pressure and anal sphincter pressure allows for the sensing of specific anorectal phases, including baseline resting, anal sphincter squeezing, and bearing down, since these anorectal phases require both rectal pressure and anal sphincter pressure to be sensed for an accurate determination of the level of success of each of these anorectal phases.

Further, the anorectal biofeedback provided by use of the pressure sensing device 10 within the pressure sensing system facilitates provision and monitoring of a training regime for treating bowel problems in the user. The pressure sensing system comprising device 10 and computer 48 allows the user the flexibility to complete anorectal training either in the presence of the health professional or in the comfort of their own home, due to the ease of use of device 10 and the ease of accessibility of such a computer 48, which may be a smartphone or tablet computing device, to receive and process pressure data from the pressure sensing device 10. This flexibility is also helpful for users who reside in rural or remote communities, with decreased access to health professionals.

It will be appreciated by persons skilled in the art that features of the above described embodiments may be combined. For example, device 10 of FIG. 8 may include an inflatable element similar to that described with reference to device 10 of FIG. 7. It will be appreciated by persons skilled in the art that numerous variations and/or modifications may be made to the above-described embodiments, without departing from the broad general scope of the present disclosure. For example, any of the embodiments of device 10 described above may comprise additional pressure sensors. The present embodiments are, therefore, to be considered in all respects as illustrative and not restrictive.

The invention claimed is:

1. A pressure sensing system, comprising:

an artificial pressure sensing device comprising an elongate housing configured to be at least partially inserted into a user, the elongate housing defining an external surface and having a proximal end and a distal end defining a longitudinal axis therebetween, the distal end being the leading end of the elongate housing in a direction of insertion of the elongate housing into the user;

a first pressure sensor configured to sense first pressure applied to a first portion of the external surface and to convert the sensed first pressure to first pressure data; and a second pressure sensor configured to sense second pressure applied to a second portion of the external surface and to convert the sensed second pressure to second pressure data, the second pressure sensor spaced, along the longitudinal axis, toward the distal end from the first pressure sensor;

a computer configured to receive and process the first pressure data and the second pressure data from the pressure sensing device;

wherein the processing of the pressure data by the computer comprises processing to assess the magnitude of pressure applied to the first and second pressure sensors and the timing of pressure applied to the first and second pressure sensors, and wherein the processing of the pressure data by the computer comprises processing to determine whether the magnitude and timing of pressure applied to the first and second pressure sensors meets predetermined criteria, the predetermined criteria at least comprising whether pressure data obtained simultaneously by the first pressure sensor and the second pressure sensor indicates that the magnitude of the first pressure applied to the first pressure sensor is within a first pressure range and that the magnitude of the second pressure applied simultaneously to the second pressure sensor is within a second pressure range; and a user interface associated with the computer and configured to present, to the user, information associated with the first pressure data and the second pressure data received from the pressure sensing device, wherein the information associated with the first pressure data and the second pressure data received from the pressure sensing device comprises information on whether, based on the processing of the pressure data by the computer, the first pressure data and the second pressure data indicates that the magnitude and timing of pressure applied to the first and second sensors meets the predetermined criteria, wherein:

the first pressure sensor is configured to sense anal sphincter pressure applied to the first portion of the external surface;

the second pressure sensor is configured to sense rectal pressure applied to the second portion of the external surface;

the first portion has a length, measured along the longitudinal axis, of between 1 cm and 6 cm;

the spacing, along the longitudinal axis, between a center of the first portion and a center of the second portion is between 3 cm and 8 cm;

the external surface of the portion of the elongate housing that is configured to be at least partially inserted into the user is cylindrical;

a length of the second portion, measured along the longitudinal axis, is defined by a pressure pad associated therewith, the pressure pad associated with the second portion being configured to move in a radial direction toward an interior of the elongate housing to transfer the second pressure to the second pressure sensor, the pressure pad associated with the second portion being sufficiently rigid not to deform in response to application of the second pressure thereto;

the first pressure sensor is located radially inwardly of the first portion; and responsive to application of the first pressure, the first portion is configured to move in a radial direction toward the first pressure sensor to mechanically transfer the first pressure to the first pressure sensor.

2. The pressure sensing system according to claim 1, further comprising a transmitter carried by the elongate housing, the transmitter being configured to transmit the first pressure data and the second pressure data.

3. The pressure sensing system according to claim 2, wherein the transmitter is configured to wirelessly transmit the first pressure data and the second pressure data.

4. The pressure sensing system according to claim 1, wherein the external surface of the elongate housing has a shape that causes the first pressure sensor to automatically align with the user's anal sphincter upon insertion of the elongate housing into the user.

5. The pressure sensing system according to claim 1, comprising a flange extending outwardly in a direction transverse to the longitudinal axis, the flange being configured to abut a portion of the user upon insertion of the elongate housing into the user and thereby to limit the extent of insertion of the elongate housing into the user.

6. The pressure sensing system of claim 5, wherein the position, along the longitudinal axis, of the flange relative to the first pressure sensor is such that, in use, abutment of the flange with the portion of the user facilitates alignment of the first pressure sensor with the user's anal sphincter.

7. The pressure sensing system of claim 1, further comprising an inflatable element carried by the distal end of the elongate housing.

8. The pressure sensing system according to claim 1, wherein the computer is further configured to receive data inputs from the user and to process the received data inputs, wherein the received data inputs comprise at least one of: food intake of the user; water intake of the user; physical exercise performed by the user; and properties of stools produced by the user.

9. The pressure sensing system of claim 1, wherein the predetermined criteria comprise at least one of the following criteria:

pressure data obtained simultaneously by the first pressure sensor and the second pressure sensor indicates that the magnitude of the first pressure applied to the first pressure sensor is between 100-180 mmHg and that the magnitude of the second pressure applied simultaneously to the second pressure sensor is in a range indicative of a resting pressure for a cavity of the user in which the second pressure sensor is located; and/or pressure data obtained simultaneously by the first pressure sensor and the second pressure sensor indicates that the magnitude of the first pressure applied to the first pressure sensor is between 20-60 mmHg and that the magnitude of the second pressure applied simultaneously to the second pressure sensor is between 60-120 mmHg.

10. The pressure sensing system of claim 1, wherein the length of the second portion is up to 3 cm.

11. The pressure sensing system of claim 1, wherein the length of the second portion is in a range from 1 cm to 3 cm.

12. The pressure sensing system of claim 1, wherein the first pressure sensor comprises a solid-state pressure sensor and a transducer.

13. The pressure sensing system of claim 1, wherein the second pressure sensor comprises a solid-state pressure sensor and a transducer.

14. The pressure sensing system of claim 1, wherein the pressure pad associated with the second portion is resiliently biased away from the second pressure sensor to cause the second pressure pad to return to an at rest configuration upon removal of external pressure applied to the second portion.

15. The pressure sensing system of claim 1, wherein the predetermined criteria at least further comprises whether pressure data obtained by the first pressure sensor and the second pressure sensor indicates coordination of maximum rectal pressure with minimum anal sphincter pressure.

* * * * *